United States Patent [19]

Kleemann et al.

[11] 4,224,226
[45] Sep. 23, 1980

[54] PROCESS FOR THE PRODUCTION OF N-SUBSTITUTED α-KETOCARBOXYLIC ACID AMIDES

[75] Inventors: Axel Kleemann; Herbert Klenk; Heribert Offermanns, all of Hanau; Paul Scherberich, Dietzenbach; Werner Schwarze, Frankfurt, all of Fed. Rep. of Germany

[73] Assignee: Deutsche Gold- und Silber-Scheideanstalt vormals Roessler, Frankfurt, Fed. Rep. of Germany

[21] Appl. No.: 926,322

[22] Filed: Jul. 20, 1978

[30] Foreign Application Priority Data

Jul. 22, 1977 [DE] Fed. Rep. of Germany ....... 2733181

[51] Int. Cl.³ ................. C07C 102/08; C07D 307/54
[52] U.S. Cl. ................. 260/347.3; 260/557 R; 260/558 R; 260/559 R; 260/561 R; 260/561 K
[58] Field of Search ............ 260/347.3, 557 R, 558 R, 260/559 R, 561 R, 561 K

[56] References Cited

U.S. PATENT DOCUMENTS

| 3,257,420 | 6/1966 | Szarvasi et al. ............... 260/347.3 X |
| 4,096,184 | 6/1978 | Nakamura et al. .......... 260/557 R X |

FOREIGN PATENT DOCUMENTS

| 1542873 | 7/1970 | Fed. Rep. of Germany. |
| 2165554 | 12/1971 | Fed. Rep. of Germany. |
| 2208568 | 9/1972 | Fed. Rep. of Germany. |
| 1795784 | 1/1976 | Fed. Rep. of Germany. |

OTHER PUBLICATIONS

Ritter et al., Journal of the American Chemical Society, vol. 70, (1948), pp. 4045 to 4050.
Ugi et al., Chem. Ber., vol 94, (1961), pp. 1116 to 1121.

*Primary Examiner*—Richard Raymond
*Attorney, Agent, or Firm*—Cushman, Darby & Cushman

[57] ABSTRACT

Compounds are prepared of the formula

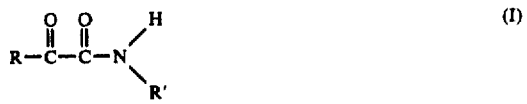
(I)

where R' is a t-alkyl group having 4 to 18 carbon atoms, preferably t-butyl, t-amyl or t-octyl and R is a straight or branched chain alkyl group with 1 to 18 carbon atoms, preferably 1 to 10 carbon atoms or an alkyl group substituted with one or more phenyl groups or a halogen atom, particularly a chlorine atom, or a cycloalkyl group with 3 to 8 carbon atoms, particularly cyclopropyl, which can be substituted by one or more 1 to 3 carbon atom alkyl groups or one or more halogen atoms, preferably chlorine, or phenyl or naphthyl or a five membered heterocyclic group or such phenyl, naphthyl or heterocyclic group substituted by halogen atoms, nitro groups, alkyl or alkoxy with 1 to 5 carbon atoms by condensing in acid medium an acyl cyanide of the formula

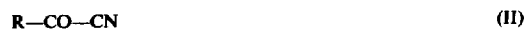

R—CO—CN (II)

where R is as defined above with either
(a) a tertiary alcohol of the formula

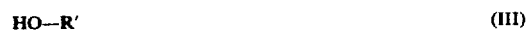

HO—R' (III)

in which R' is as defined above, or preferably
(b) an alkene of the formula

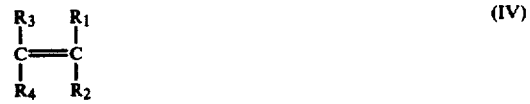
(IV)

where R₁ and R₂ are the same or different and are hydrogen or an alkyl group and wherein R₃ and R₄ are the same or different and wherein the alkyl groups in each case can be 1 to 15 carbon atoms. Some of the compounds are new. They are useful as intermediates for synthesizing herbicides and can be used directly as fungicides.

16 Claims, No Drawings

PROCESS FOR THE PRODUCTION OF N-SUBSTITUTED α-KETOCARBOXYLIC ACID AMIDES

BACKGROUND OF THE INVENTION

The invention is directed to a new process for the production of compounds, some new and some old, which are N-substituted α-ketocarboxylic acid amides of the formula

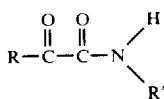

It is known that these amides can be produced by the addition of acid chlorides to the highly toxic and exceptionally nauseating smelling isonitriles with formation of carbamic acid chlorides and hydrolysis to the ketocarboxylic acid amides. This process produces, for example, for pivaloyl chloride and t-butyl isocyanide no significant yields (I. Ugi, V. Fetzer, Chem. Ber., Volume 94, pages 1116–1121 (1961)).

It is further known that such amides can be produced by the oxidation of the corresponding hydroxyamide with expensive and toxic heavy metal oxides (German OS No. 2,208,568).

SUMMARY OF THE INVENTION

It has now been found that there can be prepared compounds of the formula

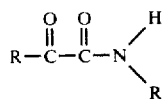

where R' is a t-alkyl group having 4 to 18 carbon atoms, preferably t-butyl, t-amyl or t-octyl and R is a straight or branched chain alkyl group with 1 to 18 carbon atoms, preferably 1 to 10 carbon atoms or an alkyl group substituted with one or more phenyl group or a halogen atom, particularly a chlorine atom, or a cycloalkyl group with 3 to 8 carbon atoms, particularly cyclopropyl, which can be substituted by one or more 1 to 3 carbon atom alkyl groups or one or more halogen atoms, preferably chlorine, or phenyl or naphthyl or a five membered heterocyclic group or such phenyl, naphthyl or heterocyclic group substituted by halogen atoms, nitro groups, alkyl or alkoxy with 1 to 5 carbon atoms by condensing in acid medium an acyl cyanide of the formula

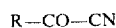   R—CO—CN   (II)

where R is as defined above with either (a) a tertiary alcohol of the formula

   HO—R'   (III)

in which R' is as defined above, or preferably (b) an alkene of the formula

where $R_1$ and $R_2$ are the same or different and are hydrogen or an alkyl group and wherein $R_3$ and $R_4$ are the same or different and wherein the alkyl groups in each case can be 1 to 15 carbon atoms.

In addition to the compounds mentioned in the specific examples, other examples of compounds within the invention include trimethyl pyruvic acid-N-t-decyl amide, trimethyl pyruvic acid-N-t-octadecylamide, 3-chlorophenylglyoxylic acid-N-t-butylamide, 2,4-dichlorophenylglyoxylic acid-N-t-amylamide, 3-nitrophenylglyoxylic acid-N-t-butylamide, 2,4-dimethylphenylglyoxylic acid-N-t-butylamide, 4-bromophenylglyoxylic acid-N-t-butylamide, 4-fluorophenylglyoxylic acid N-t-butylamide, alpha-naphthylglyoxylic acid-N-t-butylamide, beta-naphthyl-glyoxylic acid-N-t-amylamide, 5-methylfuryl-glyoxylic acid-N-t-butylamide, 2-ethylphenyl-glyoxylic acid-N-t-butylamide, 4-t-butylphenylglyoxylic acid-N-t-butylamide, 4-amylphenylglyoxylic acid-N-t-butylamide, 2,4-dimethylphenylglyoxylic acid-N-t-amylamide, 2-methoxyphenylglyoxylic acid-N-t-butylamide, 4-ethoxyphenylglyoxylic acid-N-t-butylamide, 2-amyloxyphenylglyoxylic acid-N-t-butylamide, benzylglyoxylic acid-N-t-butylamide, benzylglyoxylic acid-N-t-amylamide, diphenylmethylglyoxylic acid-N-t-amylamide, dibenzylmethylglyoxylic acid-N-t-butylamide, phenylethylglyoxylic acid-N-t-amylamide, methylglyoxylic acid-N-t-amylamide, 4-chlorobenzylglyoxylic acid-N-t-butylamide, 4-methylbenzylglyoxylic acid-t-butylamide, t-amylglyoxylic acid-N-t-butylamide, n-decylglyoxylic acid-N-t-butylamide, chloropyruvic acid-N-t-butylamide, cyclohexyl-glyoxylic acid-N-t-butylamide, cyclopentyl-glyoxylic acid-N-t-butylamide, (2,2-dibromocyclopropyl)-glyoxylic acid-N-t-butylamide, cyclooctyl-glyoxylic acid-N-t-butylamide, (1-isopropyl-cyclopropyl)-glyoxylic acid-N-t-butylamide, (1-propylcyclopropyl)-glyoxylic acid-N-t-amylamide, (1-ethylcyclopropyl)-glyoxylic acid-N-t-amylamide.

Illustrative of compounds of formula II in addition to those mentioned in the specific examples are m-chlorobenzoyl cyanide, 2,4-dichlorobenzoyl cyanide, 3-nitrobenzoyl cyanide, 2,4-dimethylbenzoyl cyanide, 4-bromobenzoyl cyanide, 4-fluorobenzoyl cyanide, alpha-naphthoyl cyanide, beta-naphthoyl cyanide, 5-methylfuroyl cyanide, 2-ethylbenzoyl cyanide, 4-t-butylbenzoyl cyanide, 4-amylbenzoyl cyanide, 2-methoxybenzoyl cyanide, 4-ethoxy benzoyl cyanide, 2-amyloxybenzoyl cyanide, phenylacetyl cyanide, diphenylacetyl cyanide, phenylpropionyl cyanide, 4-chlorophenylacetyl cyanide, 4-methylphenylacetyl cyanide, t-hexanoyl cyanide, undecanoyl cyanide, chloroacetyl cyanide, cyclohexanoxyl cyanide, cyclopentanoyl cyanide, 2,2-dibromocyclopropyl carboxylic acid cyanide, cyclooctyl carboxylic acid cyanide, 1-isopropylcyclopropyl carboxylic acid cyanide, 1-propylcyclopropyl carboxylic acid cyanide, and 1-ethylcyclopropyl carboxylic acid cyanide.

As alcohols of formula III, there can be used, for example, t-butanol, t-octanol, t-octadecanol, t-dodecanol, t-pentanol and t-hexanol.

As alkenes of formula IV, there can be used, for example, 2-methylbutene-2,diisobutylene; isobutylene, 2-methyl-heptadecene-1,2-ethylhexene-1,3-methyl-hexene-2 and 2-methylheptene-2.

The α-ketocarboxylic acid amides produced by the process of the invention in some cases are new. Both the new and old compounds can be used as intermediate products for the synthesis of herbicides. For example, they can be converted into 1,2,4-triazinones in the manner described in German OS No. 2,165,554 by reaction with, e.g., thiocarbohydrazide in the presence of a polar solvent such as an alcohol, water, dimethyl sulfoxide, dimethyl formamide, etc., and in a given case in the presence of an acid catalyst such as hydrochloric acid or sulfuric acid. Subsequently, the sulfur atom can be methylated. Thus the compounds of the invention can be reacted to herbicidally active 1,2,4-triazinones in the manner described in Klenk U.S. application Ser. No. 924,062, filed on July 12, 1978 corresponding to German application P 27 33 180.2-42, the entire disclosure of the Klenk U.S. application is hereby incorporated by reference and relied upon.

They can be converted in the manner taught in German OS No. 2,165,554 or the Klenk U.S. application to form the triazinones of the formula

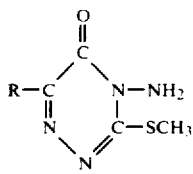

(V)

where R is as defined above. Such compounds as stated are herbicides. Many of them are disclosed in German AS No. 1,795,784 and the compounds of the formula V can be used as pre-emergent and post-emergent herbicides in the same manner as shown in examples A and B of that German AS. They can be applied to kill wheat, cotton, rice, oats, barley, corn, mustard, cress, chickweed, camomile, etc.

The compounds of the invention can also be used directly as fungicides.

The α-ketocarboxylic acid amides besides can be converted by known hydrolysis methods into the free α-ketocarboxylic acids which in part are important metabolism intermediate products as precursors of the α-aminoacids.

Within the invention, the following compounds are preferably produced: cyclopropylglyoxalic acid-N-tert. butylamide, α-methylcyclopropyl-glyoxalic acid-N-tert. butylamide and α-methyldichlorocyclopropylglyoxalic acid-N-tert. butylamide.

The reaction of the acyl cyanide of general formula (II) with the tertiary alcohol of general formula (III) or the alkene of general formula (IV) takes place under the conditions of the so-called "Ritter Reaction" of "Graf Ritter Reaction" (J.A.C.S. Volume 70, pages 4045, et seq. (1948); J.A.C.S. Volume 70, pages 4048, et seq. (1948); Methodicum Chimicum, Volume 6 (1974)) page 770. It is completely surprising that the quite unstable acyl cyanides are able to carry over this reaction since it was much more to be expected that as a result of the acid treatment there would be a splitting off of hydrocyanic acid.

The reaction can be carried out in the absence of a solvent, but is suitably undertaken in the presence of an organic solvent. Glacial acetic acid and dichloromethane are particularly suitable. Other useful solvents include, for example, higher ethers such as dibutyl ether, diisopropyl ether, dipropyl ether or diamyl ether or acetic anhydride.

The reaction temperature can be varied within wide limits. The preferred temperatures are between −20° C. and +50° C.

Suitably the reactants are added in such amounts that for each mole of acyl cyanide there is employed an overstoichiometrical amount of alcohol or alkene. For example, there can be used per mole of acyl cyanide 1 to 20 moles, preferably 1.5 to 2 moles, of alcohol or alkene.

The acid is also suitably used in a slight excess amount. For example, there can be used per mole of acyl cyanide 1 to 10 moles, preferably 1.1 to 1.5 moles, of acid.

As acid there is preferably used sulfuric acid. However, there can be used other sulfonic acids, e.g., organic sulfonic acids such as benzenesulfonic acid, p-toluene sulfonic acid, methanesulfonic acid, ethanesulfonic acid, etc.

After the hydrolysis of the reaction mixture, the ketocarboxylic acid amide can be intermediately isolated by known procedures, for example, by crystallization or extraction with subsequent crystallization or distillation.

Process variant (b) (reaction with an alkene) in many cases, for example, when R is a lower alkyl group, is preferred to variant (a) (reaction with an alcohol).

The process can comprise, consist essentially of or consist of the steps set forth with the materials set forth.

Unless otherwise indicated, all parts and percentages are by weight.

DESCRIPTION OF THE PREFERRED EMBODIMENTS

EXAMPLE 1

There were present in a stirrer equipped apparatus protected against moisture, 131 grams (1.0 mole) of benzoyl cyanide, 148 grams (2.0 moles) of t-butanol and 50 ml of methylene chloride and under stirring at about +50° C. it was treated by dropwise addition 150 grams (1.5 moles) of concentrated sulfuric acid. After the end of the dropping, the mixture was post-stirred for another hour at room temperature and then the entire mixture poured on 400 grams of ice and well agitated. Subsequently, the mixture was extracted with methylene chloride and the methylene chloride solution evaporated. There resulted 195 grams of phenylglyoxylic-N-t-butylamide which corresponds to a yield of 95% based on the acyl cyanide added. The amide has a melting point of 76°-77° C.

The following compounds were produced according to the process described in Example 1 which either were precipitated analytically pure or were purified through distillation or recrystallization.

TABLE I $$R-\overset{O}{\underset{\|}{C}}-\overset{O}{\underset{\|}{C}}-NH-\overset{CH_3}{\underset{CH_3}{\overset{|}{C}}}-CH_3$$

| Compound No. | R | Yield % | C % | H % | N % | Physical Data (°C.) |
|---|---|---|---|---|---|---|
| 1 | 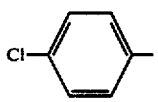 (4-Cl-C6H4–) | 95 | e 60.15<br>g 60.15 | e 5.85<br>g 6.02 | e 5.85<br>g 5.69 | M.P. 53–54° |
| 2 | 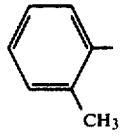 (2-CH3-C6H4–) | 95 | e 71.3<br>g 71.09 | e 7.75<br>g 7.68 | e 6.4<br>g 6.39 | M.P. 61° |
| 3 | 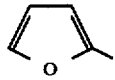 (furyl) | 95 | e 61.6<br>g 61.03 | e 6.65<br>g 6.91 | e 7.15<br>g 6.88 | M.P. 55° |
| 4 | $(CH_3)_3C-$ | 72 | e 64.83<br>g 64.79 | e 10.34<br>g 10.02 | e 7.56<br>g 7.66 | M.P. 63–65° |
| 5 | $(CH_3)_2CH-$ | 54 | — | — | — | B.P.$_{12}$ 85°<br>Lit: Kp$_{10}$ 81° |
| 6 | $(CH_3)_2CH-CH_2-$ | 70 | e 64.83<br>g 64.37 | e 10.34<br>g 10.28 | e 7.56<br>g 8.20 | B.P.$_{17}$ 98° |
| 7 | 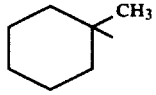 (1-methylcyclohexyl) | 76 | e 69.5<br>g 69.11 | e 10.3<br>g 10.5 | e 6.23<br>g 5.83 | M.P. 36–37° |
| 8 |  (cyclopropyl) | 71 | e 63.9<br>g 63.6 | e 8.9<br>g 8.7 | e 8.3<br>g 8.1 | M.P. 60–61° |
| 9 | 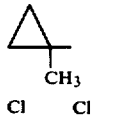 (1-methylcyclopropyl) | 99 | e 65.5<br>g 65.2 | e 9.3<br>g 9.4 | e 7.6<br>g 7.3 | M.P. 80° |
| 10 |  (2,2-dichloro-1-methylcyclopropyl) | 75 | e 47.7<br>g 47.1 | e 5.95<br>g 5.8 | e 5.56<br>5.85 | M.P. 85–86° | e = calculated
g = found

EXAMPLE 2

The procedure was the same as in Example 1 except that instead of t-butanol there were used 176 grams of t-amyl alcohol (2-methylbutanol-2).

There were isolated 210 grams of phenylglyoxalic acid-N-t-amylamide which corresponds to a yield of 96% based on the acyl cyanide employed. The amide had a melting point of 29°–30° C.

| Analysis | | |
|---|---|---|
| C % | H % | N % |
| e 71.2 | e 7.8 | e 6.3 |
| g 71.06 | g 7.97 | g 6.39 |

According to the process described in Example 2, there were produced the following compounds which were purified either through distillation or recrystallization.

TABLE II

| Compound No. | R | Yield % | Analyses C % | H % | N % | Physical Data (°C.) |
|---|---|---|---|---|---|---|
| 1 | Cl—⟨phenyl⟩— | 85 | e 61.56 g 61.60 | e 6.35 g 6.18 | e 5.52 g 5.41 | B.P.$_{0.15}$ 115° |
| 2 | ⟨phenyl⟩—, H$_3$C- | 90 | e 72.12 g 72.32 | e 8.21 g 8.13 | e 6.01 g 6.10 | B.P.$_{0.18}$ 110°–112° |
| 3 | ⟨furyl⟩ (O) | 85 | e 63.14 g 63.19 | e 7.22 g 7.46 | e 6.69 g 6.63 | M.P. 42°–43° |
| 4 | CH$_3$—C(CH$_3$)(CH$_3$)— | 73 | e 66.30 g 66.42 | e 10.62 g 10.70 | e 7.02 g 7.09 | M.P. 34°–36° |
| 5 | ⟨cyclohexyl⟩—CH$_3$ | 56 | e 70.25 g 69.32 | e 10.53 g 10.76 | e 5.84 g 6.11 | B.P.$_{14}$ 140°–142° | e = calculated
g = found

EXAMPLE 3

There were present in a stirrer apparatus protected against moisture 111 grams (1.0 mole) of pivaloyl cyanide, 150 grams (1.5 moles) of concentrated sulfuric acid and 150 ml of glacial acetic acid and there were led in during one hour under stirring at 0°–5° C. 112 grams (2.0 moles) of isobutylene. Then the mixture was warmed up to room temperature and stirred further for 4 hours. Then the mixture was poured on 500 grams of ice and after thorough stirring the precipitated amide was filtered off with suction. After the drying in the vacuum drying cabinet, there were isolated 161 grams of analytically pure trimethyl pyruvic acid-N-t-butylamide which corresponds to a yield of 87% based on the acyl cyanide employed. The amide has a melting point of 65° C.

The following compounds were produced by the process described in Example 3 which either were prepared analytically pure or were purified by distillation

TABLE III $$R-\overset{O}{\overset{\|}{C}}-\overset{O}{\overset{\|}{C}}-NH-\overset{CH_3}{\underset{CH_3}{C}}-CH_3$$

| Compound No. | R | Yield (%) | Physical Data |
|---|---|---|---|
| 1 | ⟨phenyl⟩ | 95 | M.P. 77° |
| 2 | CH$_3$— | 61 | B.P.$_{12}$ 69°–71° |
| 3 | H$_3$C\CH/H$_3$C | 72 | B.P.$_{12}$ 85° |

TABLE III-continued $$R-\overset{O}{\overset{\|}{C}}-\overset{O}{\overset{\|}{C}}-NH-\overset{CH_3}{\underset{CH_3}{C}}-CH_3$$

| Compound No. | R | Yield (%) | Physical Data |
|---|---|---|---|
| 4 | ⟨cyclohexyl⟩—CH$_3$ | 90 | M.P. 37° |

EXAMPLE 4

The procedure was the same as in Example 3 except that instead of introducing isobutylene there were dropped in 140 grams (2.0 moles) of 2-methylbutene-2. There were isolated 169 grams of trimethyl pyruvic acid-N-t-amylamide which corresponds to a yield of 85% based on the acyl cyanide employed. The amide had a melting point of 36° C.

EXAMPLE 5

The procedure was the same as in Example 4 except that in place of pivaloyl cyanide there were used 69 grams (1.0 mole) of acetyl cyanide. After the reaction mixture is poured on ice, the solution is extracted with ether, the ether subsequently evaporated and the residue fractionally distilled.

There were isolated 88 grams of pyruvic acid-N-t-amylamide which corresponds to a yield of 56% based on the acyl cyanide employed. The amide has a boiling point of 79° C. at 14 Torr.

| Analysis: | | |
|---|---|---|
| C % | H % | N % |
| e 60.7 | e 9.6 | e 8.85 |

EXAMPLE 6

The process was the same as that described in Example 3 except that instead of leading in isobutylene there were dropped in 224 grams (2.0 moles) of 2,4,4-trimethylpentene-2 (β-diisobutylene. After the mixture was poured onto ice, it was extracted with methylene chloride and the organic phase subsequently evaporated on the rotary evaporator at a water jet vacuum and 70° C. bath temperature. There resulted 125 grams of an oil which crystallized in the refrigerator. This corresponds to a yield of 52% based on the added acyl cyanide. The trimethyl pyruvic acid-N-t-octylamide had a melting point of 20°-21° C.

| Analysis: | | |
|---|---|---|
| C % | H % | N % |
| Calc. 69.66 | Calc. 11.27 | Calc. 5.80 |
| found 69.22 | found 11.42 | found 5.78 |
| NMR: in Deuterochloro- | S 1.77 δ (2H) | N-H: 6.85 δ |
| form/Tetramethyl- | S 1.42 δ (6H) | |
| silane | S 1.3 δ (9H) | |
| | S 0.98 δ (9H) | |

What is claimed is:

1. A process for the preparation of a compound having the formula $$R-\overset{O}{\underset{\|}{C}}-\overset{O}{\underset{\|}{C}}-N\overset{H}{\underset{R'}{\diagdown}}$$  (I)

where R' is a t-alkyl group having 4 to 18 carbon atoms and R is an alkyl group having 1 to 18 carbon atoms, a substituted alkyl group having 1 to 18 carbon atoms wherein the substituents are phenyl or halogen, a cycloalkyl group having 3 to 8 carbon atoms, a substituted cycloalkyl group wherein the substituents are 1 to 3 carbon atom alkyl or halogen, a five membered heterocyclic group, phenyl or naphthyl or substituted phenyl, naphthyl or five membered heterocyclic group wherein the substituents are halogen, nitro, 1 to 5 carbon atom alkyl or 1 to 5 carbon atom alkoxy comprising condensing in acid medium an acyl cyanide of the formula

R—CO—CN  (II)

with either
(a) a tertiary alcohol of the formula

HO—R'  (III)

or
(b) an alkene of the formula $$\begin{array}{cc} R_3 & R_1 \\ | & | \\ C{=}\!\!=\!\!C \\ | & | \\ R_4 & R_2 \end{array}$$  (IV)

where $R_1$ and $R_2$ are hydrogen or alkyl and $R_3$ and $R_4$ are alkyl, the alkyl groups in (IV) containing 1 to 15 carbon atoms.

2. A process according to claim 1 wherein when R is heterocyclic it is furyl.

3. A process according to claim 2 wherein when R is substituted phenyl, naphthyl or heterocyclic the substituent is 1 to 5 carbon atom alkyl or chlorine and when R is substituted alkyl the substituent is chlorine or 1 to 2 phenyl groups.

4. A process according to claim 3 wherein R is alkyl of 1 to 18 carbon atoms, cyclopropyl, cyclopropyl substituted by a 1 to 3 carbon atom alkyl group, cyclopropyl substituted by 1 to 2 chlorine atoms, cyclopropyl substituted by both a 1 to 3 carbon atom alkyl group and 1 to 2 chlorine atoms, cyclohexyl, cyclohexyl substituted by a 1 to 3 carbon atom alkyl group, phenyl, 1 to 5 carbon atom alkyl phenyl or furyl.

5. A process according to claim 4 wherein R' is t-butyl, t-amyl or t-octyl.

6. A process according to claim 4 wherein R is alkyl of 1 to 10 carbon atoms.

7. A process according to claim 4 wherein R is cyclopropyl, methyl cyclopropyl, dichlorocyclopropyl or methyl mono or di chloro cyclopropyl.

8. A process according to claim 4 wherein R is phenyl, tolyl or chlorophenyl.

9. A process according to claim 4 wherein R is furyl.

10. A process according to claim 1 wherein the reaction is carried out at −20° C. to +50° C.

11. A process according to claim 1 wherein there is employed the compound

HO—R'  (III)

12. A process according to claim 11 wherein R' has 1 to 10 carbon atoms.

13. A process according to claim 12 wherein R' is t-butyl, t-amyl or t-octyl.

14. A process according to claim 1 wherein there is employed $$\begin{array}{cc} R_3 & R_1 \\ | & | \\ C{=}\!\!=\!\!C \\ | & | \\ R_4 & R_2 \end{array}$$  (IV)

15. A process according to claim 14 wherein R is alkyl of 1 to 10 carbon atoms.

16. A process according to claim 15 wherein (IV) is isobutylene, diisobutylene or 2-methylbutene-2.

* * * * *